US009393289B2

(12) United States Patent
Metzner et al.

(10) Patent No.: US 9,393,289 B2
(45) Date of Patent: Jul. 19, 2016

(54) USE OF SULFATED GLYCOSAMINOGLYCANS FOR IMPROVING THE BIOAVAILABILITY OF FACTOR VIII

(71) Applicant: CSL BEHRING GMBH, Marburg (DE)

(72) Inventors: Hubert Metzner, Marburg (DE); Sabine Zollner, Muri (CH)

(73) Assignee: CSL Behring GmbH, Marburg (DE)

( * ) Notice: Subject to any disclaimer, the term of this patent is extended or adjusted under 35 U.S.C. 154(b) by 0 days.

(21) Appl. No.: 14/352,540

(22) PCT Filed: Oct. 18, 2012

(86) PCT No.: PCT/EP2012/070615
§ 371 (c)(1),
(2) Date: Apr. 17, 2014

(87) PCT Pub. No.: WO2013/057167
PCT Pub. Date: Apr. 25, 2013

(65) Prior Publication Data
US 2014/0315815 A1 Oct. 23, 2014

Related U.S. Application Data

(60) Provisional application No. 61/548,606, filed on Oct. 18, 2011.

(30) Foreign Application Priority Data

Oct. 18, 2011 (EP) .................................... 11185648

(51) Int. Cl.
*A61K 38/00* (2006.01)
*C07K 16/00* (2006.01)
*A61K 38/37* (2006.01)
*A61K 47/36* (2006.01)
*A61K 9/00* (2006.01)
*A61K 47/42* (2006.01)

(52) U.S. Cl.
CPC .............. *A61K 38/37* (2013.01); *A61K 9/0019* (2013.01); *A61K 47/36* (2013.01); *A61K 47/42* (2013.01)

(58) Field of Classification Search
CPC ... A61K 38/37; A61K 38/1709; A61K 38/36; C07K 14/745
See application file for complete search history.

(56) References Cited

U.S. PATENT DOCUMENTS

| 4,757,006 A | 7/1988 | Toole, Jr. et al. | |
|---|---|---|---|
| 4,868,112 A | 9/1989 | Toole, Jr. | |
| 2002/0132306 A1 | 9/2002 | Kaufman et al. | |
| 2009/0247459 A1* | 10/2009 | Schwarz et al. | 514/12 |

FOREIGN PATENT DOCUMENTS

| EP | 0 503 991 A1 | 9/1992 |
|---|---|---|
| EP | 0784632 B1 | 7/1997 |
| WO | WO 95/01804 | 1/1995 |
| WO | WO 95/26750 | 10/1995 |
| WO | WO 97/40145 | 10/1997 |
| WO | WO 00/24759 | 5/2000 |
| WO | WO 02/102850 A2 | 12/2002 |
| WO | WO 2004/067566 A1 | 8/2004 |
| WO | WO 2004/101740 A2 | 11/2004 |
| WO | WO 2009/108806 A1 | 9/2009 |
| WO | WO 2011/020866 A2 | 2/2011 |
| WO | WO 2011/095604 A1 | 8/2011 |
| WO | WO 2011095604 A1 * | 8/2011 |

OTHER PUBLICATIONS

Hirsh et. al. Guide to Anticoagulant Therapy, Circulation. 1994; 89: 1449-1468.*
HFA, Hemophelia Inheritance, http://www.hemophiliafed.org/bleeding-disorders/hemophilia/causes/, last visited May 1, 2015.*
The Diagnosis, Evaluation, and Management of von Willebrand Factor Disease, NIH Publication No. 08-5832 Dec. 2007, p. 5, spanning col. 1-2.*
Notification Concerning Transmittal of International Report on Patentability and International Preliminary Report on Patentability, issued by The International Bureau of WIPO in International Application No. PCT/EP2012/070615, mailed May 1, 2014, 8 pages.
Kaufman, R., "Expression and Structure-Function Properties of Recombinant Factor VIII", Transfusion Medicine Reviews, vol. VI, No. 4, pp. 235-246 (1992).
Fischer, B.,et al., "Structural analysis of recombinant von Willebrand factor: identification of hetero- and homo-dimers", FEBS Lett. vol. 351, pp. 345-348 (1994).
Ruggeri, Z.M., et al., "Structure and Function of von Willebrand Factor", Thromb. Haemost., vol. 82(2), pp. 576-584 (1999).
Rizza, C., et al., "Coagulation Assay of VIIIC and IXC", in Bloom ed. The Hemophilias, Churchill Livingston, NY, pp. 18-38 (1992).
Rosen, S., "Assay of Factor VIII:C with a Chromogenic Substrate", Scand J. Haematol, vol. 33, pp. 139-145 (1984).
Amano, K., et al., "Mutation at either Arg336 or Arg562 in Factor VIII is Insufficient for Complete Resistance to Activated Protein C (APC)-mediated Inactivation: Implications for the APC Resistance Test", Thromb. Haemost, vol. 79, pp. 557-563 (1998).
Swaroop, M., et al., "Mutagenesis of a Potential Immunoglobulin-binding Protein-binding Site Enhances Secretion of Coagulation Factor VIII", The Journal of Biological Chemistry, Vo. 272, No. 39, pp. 24121-24124 (1997).

(Continued)

*Primary Examiner* — Jeanette Lieb
(74) *Attorney, Agent, or Firm* — Finnegan, Henderson, Farabow, Garrett & Dunner LLP

(57) ABSTRACT

The present invention relates to pharmaceutical preparations comprising one or more Factor VIII and a sulfated glycosaminoglycan for increasing the bioavailability of Factor VIII upon non-intravenous administration. The invention further relates to the combined use of Factor VIII and a sulfated glycosaminoglycan for the treatment and prevention of bleeding disorders, whereby the bioavailability of Factor VIII is increased, and to a method for increasing the bioavailability after non-intravenous administration of Factor VIII by coadminstration of a sulfated glycosaminoglycan.

18 Claims, 1 Drawing Sheet

(56) References Cited

OTHER PUBLICATIONS

Lollar, P., "Characterization of Factor VIII B-Cell inhibitory Epitopes", Thrombosis and Haemostasis, vol. 82, pp. 505-508 (1999).

Oh, S., et al., "Synthesis of recombinant blood coagulation factor VIII (FVIII) heavy and light chains and reconstitution of active form of FVIII," Experimental and Molecular Medicine, vol. 31, No. 2, pp. 95-100 (1999).

Ananyeva, N., et al., "Catabolism of the Coagulation Factor VIII", TCM, vol. 11, No. 6, pp. 251-257 (2001).

Gale, A., et al., "Intrinsic stability and functional properties of disulfide bond-stabilized coagulation factor VIIIa variants" Journal of Thrombosis and Haemostasis, vol. 4, pp. 1315-1322 (2006).

Miao, H., et al., "Bioengineering of coagulation factor VIII for improved secretion", Blood, vol. 103, No. 9, pp. 3412-3419 (2004).

Wakabayashi, H., et al., "A Glu113Ala Mutation within a Factor VIII $Ca^{2+}$-Binding Site Enhances Cofactor Interactions in Factor Xase", Biochemistry, vol. 44, pp. 10298-10304 (2005).

Krishnan, S., et al., "Thrombin cleavage analysis of a novel antihaemophilic factor variant, factor VIII Delta II", Eur. J. Biochem, vol. 195, pp. 637-644 (1991).

Herlitschka. S., et al., "High expression of a B-domain deleted factor VIII gene in a human hepatic cell line", Journal of Biotechnology, vol. 61, pp. 165-173 (1998).

Donath, M., et al., "Characterization of des-(741-1668)-factor VIII, a single-chain factor VIII variant with a fusion site susceptible to proteolysis by thrombin and factor Xa", Biochem. J., Vo. 312, pp. 49-55 (1995).

Funderburgh, J., "Keratan sulfate: structure, biosynthesis, and function", Mini Review, Glycobiology, vol. 10, No. 10, pp. 951-958 (2000).

Gallagher, J.T., et al., "Molecular distinctions between Heparan Sulphate and Heparin: Analysis of sulphation patterns indicates Heparan Sulphate and Heparan are separate families of N-sulphated polysaccharides", Biochem. Journal, vol. 230(3), pp. 665.674 (1985).

Gallagher, J.T. et al., "Heparan Sulfate, Molecular Structure and Interactions with Growth Factors and Morphogens", In Iozzo, M.V. Proteoglycans: structure, biology and molecular interactions, Marcel Dekker Inc., New York, N.Y., pp. 27-59 (2000).

Bi, L., et al., "Targeted disruption of the mouse factor VIII gene produces a model of haemophilia A", Nature Genetics, vol. 10(1), pp. 119-121 (1995).

Bi, L., et al., "Further characterization of factor VIII-deficient mice created by gene targeted: RNA and protein studies", Blood, vol. 88(9), pp. 3446-3450 (1996).

Pipe, S., "Coagulation Factors with Improved Properties for Hemophilia Gene Therapy", Seminars in Thrombosis and Hemostasis, vol. 30, No. 2, pp. 227-237 (2004).

Collins, P.W., et al., "Factor VIII requirement to maintain a target plasma level in the prophylactic treatment of severe hemophilia A: influences of variance in pharmacokinetics and treatment regimens", Journal of Thrombosis and Haemostasis, vol. 8, pp. 269-275 (2009).

International Search Report issued by the European Patent Office in corresponding International Application No. PCT/EP2012/070615, mailed Dec. 12, 2012, 8 pages.

Written Opinion of the International Searching Authority issued by the European Patent Office in corresponding International Application No. PCT/EP2012/070615, mailed Dec. 12, 2012, 14 pages.

Björkman, S., "Prophylactic Dosing of Factor VIII and Factor IX from a Clinical Pharmacokinetic Perspective." *Haemophilia*. 9(1):101-110 (2003).

Shapiro, A.D., "Why is Primary Prophylaxis Underutilized in the United States?" *Haemophilia*. 9:670-672 (2003).

Shi, Q., et al., "Intravascular recovery of VWF and FVIII following intraperitoneal injection and differences from intravenous and subcutaneous injection in mice." *Haemophilia*. 18(4):639-646 (2012).

* cited by examiner

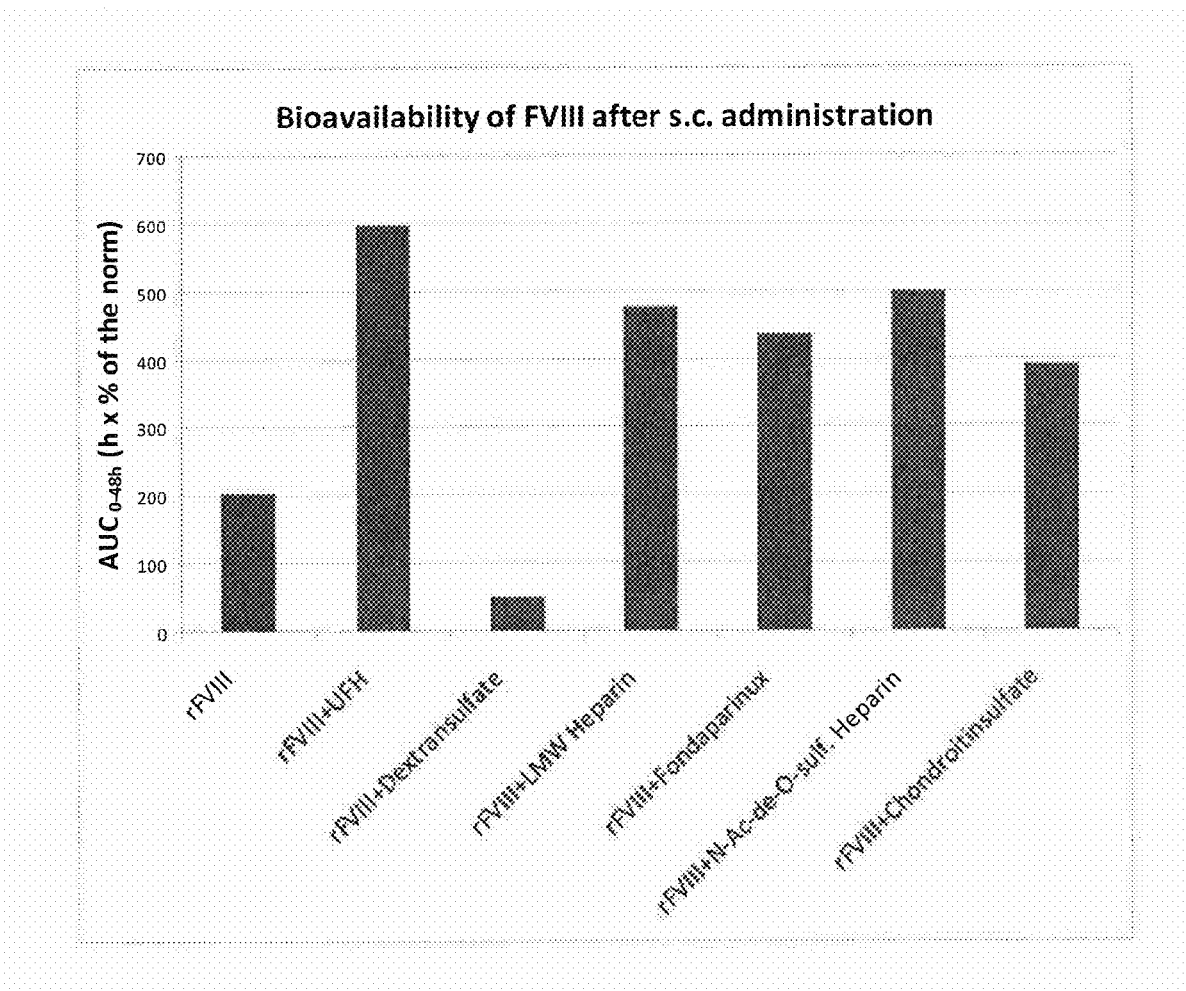

USE OF SULFATED GLYCOSAMINOGLYCANS FOR IMPROVING THE BIOAVAILABILITY OF FACTOR VIII

The present invention relates to pharmaceutical preparations comprising at least one Factor VIII and a sulfated glycosaminoglycan for increasing the bioavailability of Factor VIII upon non-intravenous administration. The invention further relates to the combined use of a Factor VIII and a sulfated glycosaminoglycan for the treatment and prevention of bleeding disorders, whereby the bioavailability of the Factor VIII is increased, and to a method for increasing the bioavailability after non-intravenous administration of a Factor VIII by co-administration of a sulfated glycosaminoglycan.

BACKGROUND OF THE INVENTION

Factor VIII (FVIII)

FVIII is a blood plasma glycoprotein of about 280 kDa molecular mass, produced in the liver of mammals. It is a critical component of the cascade of coagulation reactions that lead to blood clotting. Within this cascade is a step in which Factor IXa (FIXa), in conjunction with activated Factor VIII (FVIIIa), converts Factor X (FX) to an activated form, FXa. FVIIIa acts as a cofactor at this step, being required together with calcium ions and phospholipids for maximizing the activity of FIXa. The most common hemophilic disorder is caused by a deficiency of functional FVIII called hemophilia A.

An important advance in the treatment of Hemophilia A has been the isolation of cDNA clones encoding the complete 2,351 amino acid sequence of human FVIII (U.S. Pat. No. 4,757,006) and the provision of the human FVIII gene DNA sequence and recombinant methods for its production).

Analysis of the deduced primary amino acid sequence of human FVIII determined from the cloned cDNA indicates that it is a heterodimer processed from a larger precursor polypeptide. The heterodimer consists of a C-terminal light chain of about 80 kDa in a metal ion-dependent association with an about 200 kDa N-terminal heavy chain. (See review by Kaufman, Transfusion Med. Revs. 6:235 (1992)). Physiological activation of the heterodimer occurs through proteolytic cleavage of the protein chains by thrombin. Thrombin cleaves the heavy chain to a 90 kDa protein, and then to 54 kDa and 44 kDa fragments. Thrombin also cleaves the 80 kDa light chain into a 72 kDa protein. It is the latter protein, and the two heavy chain fragments (54 kDa and 44 kDa above), held together by calcium ions, that constitute active FVIII. Inactivation occurs when the 44 kDa A2 heavy chain fragment dissociates from the molecule or when the 72 kDa and 54 kDa domains are further cleaved by thrombin, activated protein C or FXa. In plasma, FVIII is stabilized by association with a 50-fold molar excess of Von Willebrand Factor protein ("VWF"), which appears to inhibit proteolytic destruction of FVIII as described above.

The amino acid sequence of FVIII is organized into three structural domains: a triplicated A domain of 330 amino acids, a single B domain of 980 amino acids, and a duplicated C domain of 150 amino acids. The B domain has no homology to other proteins and provides 18 of the 25 potential asparagine(N)-linked glycosylation sites of this protein. The B domain has apparently no function in coagulation and can be deleted with the B-domain deleted FVIII molecule still having procoagulant activity.

Von Willebrand Factor (VWF)

VWF is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The precursor polypeptide, pre-pro-VWF, consists of a 22-residue signal peptide, a 741-residue pro-peptide and the 2050-residue polypeptide found in mature plasma VWF (Fischer et al., FEBS Lett. 351: 345-348, 1994). Upon secretion into plasma VWF circulates in the form of various species with different molecular sizes. These VWF molecules consist of oligo- and multimers of the mature subunit of 2050 amino acid residues. VWF can be usually found in plasma as one dimer up to multimers consisting of 50-100 dimers (Ruggeri et al. Thromb. Haemost. 82: 576-584, 1999). The in vivo half-life of human VWF in the human circulation is approximately 12 hours.

The most frequent inherited bleeding disorder in humans is von Willebrand's disease (VWD). Depending on the severity of the bleeding symptoms, VWD can be treated by replacement therapy with concentrates containing VWF, in general derived from human plasma but recombinant VWF also is under development. VWF can be prepared from human plasma as for example described in EP 0503991. In patent EP 0784632 a method for isolating recombinant VWF is described.

VWF is known to stabilize FVIII in vivo and, thus, plays a crucial role to regulate plasma levels of FVIII and as a consequence is a central factor to control primary and secondary hemostasis. It is also known that after intravenous administration of pharmaceutical preparations containing VWF in VWD patients an increase in endogenous FVIII:C to 1 to 3 units per ml in 24 hours can be observed demonstrating the in vivo stabilizing effect of VWF on FVIII.

The patients in general benefit from the specific mode of action of the active ingredients but currently all commercially available Factor VIII preparations are administered via intravenous administration which involves a risk for infections at the injection site and is in general a procedure patients would like to avoid especially in the treatment of children with defects in their coagulation system.

Until today the standard treatment of Hemophilia A and VWD involves frequent intravenous infusions of preparations of FVIII and VWF concentrates. The treatment of Hemophilia B requires the biweekly administration of Factor IX and in the treatment of inhibitor patients with FVIIa, multiple administrations of FVIIa per week are used to avoid bleedings.

These replacement therapies are generally effective, however, for example in severe hemophilia A patients undergoing prophylactic treatment Factor VIII has to be administered intravenously (i.v.) about 3 times per week due to the short plasma half life of Factor VIII of about 12 hours. Already by achieving FVIII levels above 1% of normal human plasma corresponding to a raise of FVIII levels by 0.01 U/ml, severe hemophilia A is turned into moderate hemophilia A. In prophylactic therapy the dosing regime is designed such that the trough levels of FVIII activity do not fall below levels of 2-3% of the FVIII activity of non-hemophiliacs.

The administration of a Factor VIII via intravenous administration is cumbersome, associated with pain and entails the risk of an infection especially as this is mostly done in home treatment by the patients themselves or by the parents of children being diagnosed for hemophilia A. In addition, frequent intravenous injections inevitably result in scar formation, interfering with future infusions As prophylactic treatment in severe hemophilia is started early in life, with children often being less than 2 years old, it is even more difficult to inject FVIII 3 times per week into the veins of such small patients. For a limited period of time, implantation of port systems may offer an alternative. However, in these cases repeated infections may occur and ports can cause inconvenience during physical exercise.

Thus there is a great medical need to obviate the need to infuse Factor VIII intravenously.

Subcutaneous administration has been proposed for Factor VIII, e.g. in WO 95/01804 A1 and WO 95/026750. However, very high doses of Factor VIII had to be administered to achieve an acceptable bioavailability.

Another approach to improve the bioavailability upon non-intravenous administration has been to use albumin-fused Factor VIII (WO 2011/020866 A2).

It is highly desirable to improve the bioavailability of Factor VIII upon non-intravenous administration. The inventors of this application surprisingly found that the bioavailability of Factor VIII is substantially increased if it is administered together with sulfated glycosaminoglycans.

SUMMARY OF THE INVENTION

In a first aspect the present invention therefore relates to a Factor VIII for use in the treatment or prevention of a bleeding disorder, said treatment or prevention comprising the non-intravenous injection of said Factor VIII and of a sulfated glycosaminoglycan, In a further aspect, the present invention therefore relates to a Factor VIII for use in the treatment or prevention of a bleeding disorder, said treatment or prevention comprising the non-intravenous injection of said Factor VIII and of a sulfated glycosaminoglycan, wherein, during a period from 2 hours after injection to 48 hours after injection, the plasma level of the Factor VIII in the treated subject is continuously higher than 2% of the normal plasma level of the Factor VIII in healthy subjects when the Factor VIII is administered subcutaneously at a dose of 50 to 1000 IU/kg body weight.

A preferred embodiment of this aspect is a Factor VIII for use in the treatment or prophylaxis of hemophilia A in a human individual, said treatment or prophylaxis comprising the administration of said Factor VIII and of a sulfated glycosaminoglycan by subcutaneous, intradermal or intramuscular injection, wherein, during a period from 2 hours after injection to 48 hours after injection, the plasma level of the Factor VIII in the human individual is continuously higher than 2% of the normal plasma level of the Factor VIII in healthy human individuals when the Factor VIII is administered subcutaneously at a dose of 50 to 1000 IU/kg body weight.

Another aspect of the invention is a Factor VIII for use in the treatment or prophylaxis of a bleeding disorder in a human individual, said treatment or prophylaxis comprising the administration of said Factor VIII and of a sulfated glycosaminoglycan by subcutaneous, transdermal or intramuscular injection, wherein the relative bioavailability of the Factor VIII in the human individual is at least 20% higher than that of the Factor VIII administered in the same manner without sulfated glycosaminoglycan.

A preferred embodiment of this aspect is a Factor VIII for use in the treatment or prophylaxis of hemophilia A in a human individual, said treatment or prophylaxis comprising the administration of said Factor VIII and of a sulfated glycosaminoglycan by subcutaneous, intradermal or intramuscular injection, wherein the relative bioavailability of the Factor VIII in the human individual is at least 20% higher than that of the Factor VIII administered in the same manner without sulfated glycosaminoglycan.

In a third aspect, the invention relates to a sulfated glycosaminoglycan for improving the bioavailability of a Factor VIII.

In a further aspect, the invention relates to a sulfated glycosaminoglycan for improving the bioavailability of a Factor VIII, wherein said sulfated glycosaminoglycan and said Factor VIII are administered by subcutaneous, transdermal or intramuscular injection.

A further aspect of the invention is a pharmaceutical kit for the therapy or prophylaxis of a bleeding disorder, comprising a Factor VIII and a sulfated glycosaminoglycan.

A further aspect of the invention is a method of treating or preventing a bleeding disorder, comprising administering to a subject in need thereof a therapeutically effective amount of a Factor VIII and a sulfated glycosaminoglycan so as to increase the bioavailability of the Factor VIII, wherein said administration comprises subcutaneous, transdermal or intramuscular injection.

A further aspect of the invention is a method for increasing the bioavailability of a Factor VIII, wherein a sulfated glycosaminoglycan is co-administered with said Factor VIII by subcutaneous, intradermal or intramuscular injection.

In all aspects of the invention, the Factor VIII is preferably human Factor VIII. A preferred sulfated glycosaminoglycan is heparin, most preferably the heparin is unfractionated heparin.

DESCRIPTION OF THE FIGURE

FIG. 1 depicts the results of Example 1. The bioavailability of FVIII is increased if a sulfated glycosaminoglycan is co-administered. As can be seen, dextran sulfate has no positive effect.

DETAILED DESCRIPTION

The present invention concerns the treatment and prophylaxis of bleeding disorders.

As used herein, the term "bleeding disorders" includes familial and acquired hemophilia A.

According to the first aspect of the invention a therapeutic, non-intravenous use of a Factor VIII is provided which comprises co-administration of a sulfated glycosaminoglycan.

Factor VIII may be wild-type Factor VIII polypeptides or Factor VIII polypeptides which may contain mutations. The degree and location of glycosylation or other post-translation modifications may vary depending on the chosen host cells and the nature of the host cellular environment. When referring to specific amino acid sequences, posttranslational modifications of such sequences are encompassed in this application.

The terms "Factor VIII", and FVIII" are used interchangeably herein. "Factor VIII" includes wild type Factor VIII as well as derivatives of wild type Factor VIII having the procoagulant activity of wild type Factor VIII. Derivatives may have deletions, insertions and/or additions compared with the amino acid sequence of wild type Factor VIII. The term Factor VIII includes proteolytically processed forms of Factor VIII, e.g. the form before activation, comprising heavy chain and light chain.

The term "Factor VIII" includes any Factor VIII variants or mutants having at least 10%, preferably at least 25%, more preferably at least 50%, most preferably at least 75% of the biological activity of wild type Factor VIII. A suitable test to determine the biological activity of Factor VIII is the one stage or the two stage coagulation assay (Rizza et al. 1982. Coagulation assay of FVIII:C and FIXa in Bloom ed. The Hemophilias. NY Churchchill Livingston 1992) or the chromogenic substrate FVIII activity assay (S. Rosen, 1984. Scand J Haematol 33: 139-145, suppl.). The content of these references is incorporated herein by reference.

As non-limiting examples, Factor VIII molecules include Factor VIII mutants preventing or reducing APC cleavage (Amano 1998. Thromb. Haemost. 79:557-563), albumin-fused FVIII molecules (WO 2011/020866 A2), FVIII-Fc fusion molecules (WO 04/101740 A), Factor VIII mutants further stabilizing the A2 domain (WO 97/40145), FVIII mutants resulting in increased expression (Swaroop et al. 1997. JBC 272:24121-24124), Factor VIII mutants with reduced immunogenicity (Lollar 1999. Thromb. Haemost. 82:505-508), FVIII reconstituted from differently expressed heavy and light chains (Oh et al. 1999. Exp. Mol. Med. 31:95-100), FVIII mutants reducing binding to receptors leading to catabolism of FVIII like HSPG (heparan sulfate proteoglycans) and/or LRP (low density lipoprotein receptor related protein) (Ananyeva et al. 2001. TCM, 11:251-257), disulfide bond-stabilized FVIII variants (Gale et al., 2006. J. Thromb. Hemost. 4:1315-1322), FVIII mutants with improved secretion properties (Miao et al., 2004. Blood 103: 3412-3419), FVIII mutants with increased cofactor specific activity (Wakabayashi et al., 2005. Biochemistry 44:10298-304), FVIII mutants with improved biosynthesis and secretion, reduced ER chaperone interaction, improved ER-Golgi transport, increased activation or resistance to inactivation and improved half-life (summarized by Pipe 2004. Sem. Thromb. Hemost. 30:227-237), and FVIII mutants having a deletion of all or part of the B-domain (see, e.g., WO 2004/067566 A1, WO 02/102850 A2, WO 00/24759 A1 and U.S. Pat. No. 4,868,112). Particularly preferred are FVIII molecules which are "single chain" FVIII molecules. Single chain FVIII have a deletion of all or part of the B-domain and a deletion of all or a part of the acidic a3 region, so that the cleavage site at Arg1648 (which is usually cleaved during secretion) is deleted. Single chain FVIII molecules are disclosed in, e.g., WO 2004/067566 A1; US 2002/132306 A1; Krishnan et al. (1991) European Journal of Biochemistry vol. 195, no. 3, pages 637-644; Herlitschka et al. (1998) Journal of Biotechnology, vol. 61, no. 3, pages 165-173; Donath et al. (1995) Biochem. J., vol. 312, pages 49-55.

All of these Factor VIII mutants and variants are incorporated herein by reference in their entirety.

The amino acid sequence of the mature wild type form of human Factor VIII is shown in SEQ ID NO:2. The reference to an amino acid position of a specific sequence means the position of said amino acid in the FVIII wild-type protein and does not exclude the presence of mutations, e.g. deletions, insertions and/or substitutions at other positions in the sequence referred to. For example, a mutation in "Glu2004" referring to SEQ ID NO:2 does not exclude that in the modified homologue one or more amino acids at positions 1 through 2332 of SEQ ID NO:2 are missing. A DNA sequence encoding SEQ ID NO:2 is shown in SEQ ID NO:1.

The term "glycosaminoglycan", as used herein, refers to an oligo- or polysaccharide comprising particularly aminohexose units. Sulfated glycosaminoglycans include, but are not limited to chondroitin sulfate, dermatan sulfate, keratan sulfate, heparin and heparan sulfate. Preferably, the sulfated glycosaminoglycan is heparin, most preferably, the sulfated glycosaminoglycan is unfractionated heparin.

The term "heparin" includes unfractionated heparin and heparins having a lower molecular weight. In one embodiment, the heparin used in accordance with this invention is "unfractionated heparin" which may have an average molecular weight of about 8 kDa to about 30 kDa, preferably of about 10 kDa to about 20 kDa, most preferably of about 12 kDa to about 16 kDa, e.g. about 15 kDa. In another embodiment, the heparin used in accordance with this invention is a low molecular weight heparin (LMWH). LMWHs are heparins or heparin salts having an average molecular weight of less than 8000 Da and for which at least 60% of all chains have a molecular weight less than 8000 Da. Preferably, the molecular weight of the LMWH used in accordance with this invention is about 2 kDa to about 8 kDa, more preferably about 3 kDa to about 6 kDa, most preferably of about 4 kDa to about 5 kDa, e.g. about 4.5 kDa. The LMWHs can be obtained by various methods of fractionation or depolymerisation of polymeric heparin. Examples of LMWHs include, but are not limited to, ardeparin (Normiflo), certoparin (Sandoparin), enoxaparin (Lovenox and Clexane), parnaparin (Fluxum), tinzaparin (Innohep and Logiparin), dalteparin (Fragmin), reviparin (Clivarin) and nadroparin (Fraxiparin).

The term "heparin" includes also small molecular weight fragments of heparin molecules, either derived from naturally occurring heparin by cleavage and isolation or by synthetic routes. A commercially available sulfated pentasaccharide exists for example that is manufactured synthetically and which structure is derived from heparin. It is available as Fondaparinux sodium.

Chondroitin sulfate includes, e.g., chondroitin sulfate A (chondroitin-4-sulfate), chondroitin sulfate C (chondroitin-6-sulfate), chondroitin sulfate D (chondroitin-2,6-sulfate), and chondroitin sulfate E (chondroitin-4,6-sulfate).

Dermatan sulfate (previously also called chondroitin sulfate B) is another sulfated glycosaminoglycan which is commercially available.

Keratan sulfate is another sulfated glycosaminoglycan. The structure of keratan sulfate is described in, e.g., Funderburgh (2000) Glycobiology vol. 10 no. 10 pp. 951-958.

Heparan sulfate is an N-sulfated polysaccharide which is different from Heparin (see, e.g., Gallagher, J. T., Lyon, M. (2000). "Molecular structure of Heparan Sulfate and interactions with growth factors and morphogens". In Iozzo, M, V. Proteoglycans: structure, biology and molecular interactions. Marcel Dekker Inc. New York, N.Y. pp. 27-59; and Gallagher, J. T. Walker, A. (1985). "Molecular distinctions between Heparan Sulphate and Heparin: Analysis of sulphation patterns indicates Heparan Sulphate and Heparin are separate families of N-sulphated polysaccharides". Biochem. J. 230 (3): 665-74)

In one embodiment of the invention, the plasma level of the Factor VIII in the treated subject is, during a period from 5 hours after injection to 8 hours after injection, continuously higher than 2%, preferably higher than 5%, more preferably higher than 8%, most preferably higher than 10%, of the normal plasma level of the Factor VIII in healthy subjects. The plasma level is to be determined as shown hereinafter in Example 1.

In one embodiment of the invention, the plasma level of the Factor VIII in the treated subject is, during a period from 4 hours after injection to 16 hours after injection, continuously higher than 2%, preferably higher than 5%, more preferably higher than 8%, most preferably higher than 10%, of the normal plasma level of the Factor VIII in healthy subjects.

In another embodiment of the invention, the plasma level of the Factor VIII in the treated subject is, during a period from 3 hours after injection to 24 hours after injection, continuously higher than 2%, preferably higher than 4%, more preferably higher than 6%, most preferably higher than 8%, of the normal plasma level of the Factor VIII in healthy subjects.

In another embodiment of the invention, the plasma level of the Factor VIII in the treated subject is, during a period from 2 hours after injection to 32 hours after injection, continuously higher than 2%, preferably higher than 3%, more preferably higher than 4%, most preferably higher than 5%, of the normal plasma level of the Factor VIII in healthy subjects.

In yet another embodiment of the invention, the plasma level of the Factor VIII in the treated subject is, during a period from 1 hour after injection to 48 hours after injection, continuously higher than 2%, preferably higher than 3%, more preferably higher than 4%, most preferably higher than 5%, of the normal plasma level of the Factor VIII in healthy subjects.

The above-mentioned plasma levels are preferably obtained when the Factor VIII (e.g. FVIII) is administered by subcutaneous injection at a dose of less than 1,000 IU/kg body weight, or less than 800 IU/kg body weight, or less than 600 IU/kg body weight, or less than 400 IU/kg body weight, e.g. at a dose of from about 10 IU/kg body weight to about 1,000 IU/kg body weight, or from about 20 IU/kg body weight to about 800 IU/kg body weight, or from about 30 IU/kg body weight to about 700 IU/kg body weight, or from about 40 IU/kg body weight to about 600 IU/kg body weight, or from about 50 IU/kg body weight to about 500 IU/kg body weight, or from about 75 IU/kg body weight to about 400 IU/kg body weight, or from about 100 IU/kg body weight to about 300 IU/kg body weight, or from about 50 IU/kg body weight to about 1,000 IU/kg body weight, or from about 50 IU/kg body weight to about 800 IU/kg body weight, or from about 50 IU/kg body weight to about 700 IU/kg body weight, or from about 50 IU/kg body weight to about 600 IU/kg body weight, or from about 50 IU/kg body weight to about 500 IU/kg body weight, or from about 50 IU/kg body weight to about 400 IU/kg body weight, or from about 50 IU/kg body weight to about 300 IU/kg body weight, or about 50 IU/kg body weight to about 200 IU/kg body weight.

In one embodiment, the Factor VIII and the sulfated glycosaminoglycan are contained in the same composition. This composition comprising the two components may be administered to the patient by a single injection or the like.

In another embodiment, the Factor VIII and the sulfated glycosaminoglycan are not present in the same composition. For example, each of the two components may be provided in a separate dosage form in said pharmaceutical preparation.

If the two components are not present in the same composition the separate compositions may either be administered separately, or they may be mixed shortly before administration so that the Factor VIII and the sulfated glycosaminoglycan will be administered simultaneously. If there is separate administration, the administration may be done sequentially, e.g. in a time-staggered manner. In general, it is preferred that the two components are administered simultaneously by a single administration, e.g. injection. Various routes of administration are discussed below. They apply to the above mutatis mutandis.

The components of the pharmaceutical preparation may be dissolved in conventional physiologically compatible aqueous buffer solutions to which there may be added, optionally, pharmaceutical excipients to provide the pharmaceutical preparation. The components of the pharmaceutical preparation may already contain all necessary pharmaceutical, physiologically compatible excipients and may be dissolved in water for injection to provide the pharmaceutical preparation.

Such pharmaceutical carriers and excipients as well as the preparation of suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", $3^{rd}$ edition, Kibbe et al., Pharmaceutical Press (2000)). In certain embodiments, a pharmaceutical composition can comprise at least one additive such as a filler, bulking agent, buffer, stabilizer, or excipient. Standard pharmaceutical formulation techniques are well known to persons skilled in the art (see, e.g., 2005 Physicians' Desk Reference®, Thomson Healthcare: Montvale, N.J., 2004; Remington: The Science and Practice of Pharmacy, 20th ed., Gennaro et al., Eds. Lippincott Williams & Wilkins: Philadelphia, Pa., 2000). Suitable pharmaceutical additives include, e.g., sugars like mannitol, sorbitol, lactose, sucrose, trehalose, or others, amino acids like histidine, arginine, lysine, glycine, alanine, leucine, serine, threonine, glutamic acid, aspartic acid, glutamine, asparagine, phenylalanine, or others, additives to achieve isotonic conditions like sodium chloride or other salts, stabilizers like Polysorbate 80, Polysorbate 20, Polyethylene glycol, propylene glycol, calcium chloride, or others, physiological pH buffering agents like Tris(hydroxymethyl)aminomethan, and the like. In certain embodiments, the pharmaceutical compositions may contain pH buffering reagents and wetting or emulsifying agents. In further embodiments, the compositions may contain preservatives or stabilizers. In particular, the pharmaceutical preparation comprising the Factor VIII may be formulated in lyophilized or stable soluble form. The Factor VIII may be lyophilized by a variety of procedures known in the art. Also if the sulfated glycosaminoglycan and the Factor VIII are contained in the same composition, such composition may also be provided in lyophilized or in stable soluble form. Lyophilized formulations are reconstituted prior to use by the addition of one or more pharmaceutically acceptable diluents such as sterile water for injection or sterile physiological saline solution or a suitable buffer solution.

The composition(s) contained in the pharmaceutical preparation of the invention may be delivered to the individual by any pharmaceutically suitable means. Various delivery systems are known and can be used to administer the composition by any convenient route. Preferably, the composition(s) contained in the pharmaceutical preparation of the invention are delivered to the individual by non-intravenous injection. More preferably, the composition(s) of the invention are formulated for subcutaneous, intramuscular, intraperitoneal, intracerebral, intrapulmonar, intranasal, intradermal or transdermal administration, most preferably for subcutaneous, intramuscular or transdermal administration according to conventional methods. The formulations can be administered continuously by infusion or by bolus injection. Some formulations may encompass slow release systems.

The composition(s) of the pharmaceutical preparation of the present invention is/are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

In the case of Factor VIII, the dose of one administration may be selected such that, during a period from 2 hours after injection to 48 hours after injection, the plasma level of the Factor VIII in the treated subject is continuously higher than 2%, preferably higher than 3%, more preferably higher than 4%, most preferably higher than 5%, of the normal plasma level of Factor VIII in healthy subjects.

Preferably, the dose of Factor VIII for one administration is less than 1,000 IU/kg body weight, or less than 800 IU/kg body weight, or less than 600 IU/kg body weight, or less than 400 IU/kg body weight, e.g. at a dose of from about 10 IU/kg body weight to about 1,000 IU/kg body weight, or from about 20 IU/kg body weight to about 800 IU/kg body weight, or from about 30 IU/kg body weight to about 700 IU/kg body weight, or from about 40 IU/kg body weight to about 600 IU/kg body weight, or from about 50 IU/kg body weight to about 500 IU/kg body weight, or from about 75 IU/kg body weight to about 400 IU/kg body weight, or from about 100 IU/kg body weight to about 300 IU/kg body weight, or from about 50 IU/kg body weight to about 1,000 IU/kg body weight, or from about 50 IU/kg body weight to about 800 IU/kg body weight, or from about 50 IU/kg body weight to about 700 IU/kg body weight, or from about 50 IU/kg body weight to about 600 IU/kg body weight, or from about 50 IU/kg body weight to about 500 IU/kg body weight, or from about 50 IU/kg body weight to about 400 IU/kg body weight, or from about 50 IU/kg body weight to about 300 IU/kg body weight, or about 50 IU/kg body weight to about 200 IU/kg body weight.

The Factor VIII can be administered on its own together with the sulfated glycosaminoglycan. Alternatively, the Factor VIII can be administered in association with vWF, i.e. as a FVIII/vWF complex, together with the sulfated glycosaminoglycan.

The amount of sulfated glycosaminoglycan administered typically ranges from about 0.001 to about 100 mg/mL product applied, from about 0.01 to about 10 mg/mL product applied, from about 0.05 to about 1 mg/mL product applied.

The term "bioavailability", as used herein, refers to the proportion of an administered dose of a Factor VIII (e.g. Factor VIII or a FVIII-related preparation) that can be detected in plasma at predetermined times until a final time point after subcutaneous, intravenous or intradermal administration. Typically, bioavailability is measured in test animals by administering a dose of between 10 IU/kg and 1000 IU/kg of the preparation (e.g. 400 IU/kg body weight); obtaining plasma samples at pre-determined time points after administration; and determining the content of the Factor VIII, e.g. Factor VIII or Factor VIII-related polypeptides in the samples using one or more of a chromogenic or clotting assay (or any bioassay), an immunoassay, or an equivalent thereof. The bioavailability is expressed as the area under the curve (AUC) of the concentration or activity of the Factor VIII in plasma on the y-axis and the time after administration on the x-axis until a predefined final time point after administration. Preferably, this predefined time point is 48 hours after administration. Most preferably, the bioavailability is determined as shown in Example 1 below. Relative bioavailability of a test preparation refers to the ratio between the AUC of the test preparation (e.g. Factor VIII+sulfated glycosaminoglycan) and that of the reference preparation (e.g. Factor VIII alone) which is administered in the same dose and way (e.g. intravenous, subcutaneous or intradermal) as the test preparation.

According to the present invention, the bioavailability of the Factor VIII (when co-administered with the sulfated glycosaminoglycan) is higher than that of the Factor VIII when administered alone. Preferably, the bioavailability is increased by at least 20%, more preferably by at least 50%, more preferably by at least 75%, most preferably by at least 100%. The increase in bioavailability is preferably obtained when the Factor VIII is administered by subcutaneous injection at a dose of less than 1,000 IU/kg body weight, or less than 800 IU/kg body weight, or less than 600 IU/kg body weight, or less than 400 IU/kg body weight, e.g. at a dose of from about 10 IU/kg body weight to about 1,000 IU/kg body weight, or from about 20 IU/kg body weight to about 800 IU/kg body weight, or from about 30 IU/kg body weight to about 700 IU/kg body weight, or from about 40 IU/kg body weight to about 600 IU/kg body weight, or from about 50 IU/kg body weight to about 500 IU/kg body weight, or from about 75 IU/kg body weight to about 400 IU/kg body weight, or from about 100 IU/kg body weight to about 300 IU/kg body weight, or from about 50 IU/kg body weight to about 1,000 IU/kg body weight, or from about 50 IU/kg body weight to about 800 IU/kg body weight, or from about 50 IU/kg body weight to about 700 IU/kg body weight, or from about 50 IU/kg body weight to about 600 IU/kg body weight, or from about 50 IU/kg body weight to about 500 IU/kg body weight, or from about 50 IU/kg body weight to about 400 IU/kg body weight, or from about 50 IU/kg body weight to about 300 IU/kg body weight, or about 50 IU/kg body weight to about 200 IU/kg body weight.

The pharmaceutical composition(s) of the invention may be administered alone or in conjunction with other therapeutic agents. These agents may be incorporated as part of the same pharmaceutical.

EXAMPLES

Example 1

Assessment of Bioavailability of s.c. Applied FVIII and Various Additives in a Hemophilia a Model Materials and Animal Model The Factor VIII used in the experiments was a B-domain truncated, single-chain recombinant factor VIII (hereinafter referred to as "rFVIII"). The Factor VIII was obtained by directly fusing Asn764 with Thr1653. It has been expressed in cell culture cells and purified from the cell culture medium.

The further agents used are summarized in Table 1.

TABLE 1

| Compound class | Type of compound and/or source |
|---|---|
| Unfractionated heparin | Heparin-Natrium-25000-ratiopharm |
| Low molecular weight heparin | Dalteparin (Fragmin ® from Pfizer) |
| Dextran sulfate | Ca. 500 kDa |
| Pentosan sulfate | Fondaparinux sodium (Arixtra ® from SKB) |
| N-Acetyl de-O-sulfated Heparin | N-Acetyl-de-O-sulfated heparin sodium salt from Sigma-Aldrich (Sigma product No. A6039) CAS Number 133686-69-8 |
| Chondroitin sulfate | Chondroitin sulfate A sodium salt from bovine trachea, obtained from Sigma-Aldrich (Sigma product No. C9819) CAS Number 39455-18-0 |

Factor VIII knockout mice were used as animal model for hemophilia A. These mice lack exons 16 and 17 and thus do not express FVIII (Bi L. et al, Nature genetics, 1995, Vol 10(1), 119-121; Bi L. et al, Blood, 1996, Vol 88(9), 3446-3450). This allows the analysis of FVIII levels following treatment by quantification of FVIII activity in the plasma of the ko mice.

Methods

To assess whether extravascular injections might be an option for an improved therapy with rFVIII (human), a typical representative for an extravascular therapy, subcutaneous injection, was chosen. The design of the non-clinical pharmacokinetic study performed is detailed in tables 2 and 3 below. Plasma levels of Factor VIII activity were determined following a single intravenous or subcutaneous injection of rFVIII together with various additives (detailed treatment groups in table 2) in a hemophilia A model.

Corresponding groups were treated with the same dose of FVIII (chromogenic substrate (CS) activity assay) in the presence of various different additives. For a single application the various different components for each treatment group were mixed together in a volume of 200 µL (identical volumes for all groups) prior to subcutaneous application to FVIII knockout (ko) mice weighing about 25 g. The treatment groups are summarized in table 2.

Under short term anesthesia, blood samples were drawn, anticoagulated using sodium citrate to 10% citrate blood, processed to plasma and stored at −70° C. for the determination of FVIII activity. The sampling time points are detailed in table 3. Quantification of FVIII activity in plasma was performed by a standard, aPTT based approach (Behring Coagulation Timer). The animals were kept at standard housing conditions.

TABLE 2

Treatment groups

| No. | Treatment | FVIII (CS activity assay)/Additive Dose | volume [mL/kg] | schedule | route | N |
|---|---|---|---|---|---|---|
| 1 | rFVIII | 400 IU/kg | 8 | single injection (t = 0) | s.c. | 25 |
| 2 | rFVIII/ unfractionated Heparin | 400 IU/kg/ 5 U/mL product applied | 8 | single injection | s.c. | 25 |
| 3 | rFVIII/ Dextransulfate (ca. 500 kDa) | 400 IU/kg/ 400 µg/mL product applied | 8 | single injection | s.c. | 25 |
| 4 | rFVIII/ Fragmin | 400 IU/kg/ 5 U/mL product applied | 8 | single injection | s.c. | 20 |
| 5 | rFVIII/ Fondaparinux | 400 IU/kg/ 10 µg/mL product applied | 8 | single injection | s.c. | 20 |
| 6 | rFVIII/ N-Acetyl de-O-sulfated Heparin | 400 IU/kg/ 10 µg/mL product applied | 8 | single injection | s.c. | 20 |
| 7 | rFVIII/ Chondroitin sulfate | 400 IU/kg/ 10 µg/mL product applied | 8 | single injection | s.c. | 20 |

Results

The results are summarized in Table 3 and FIG. 1. Subcutaneous injection of 400 IU/kg rFVIII in presence of various sulfated glycosaminoglycans into FVIII ko mice resulted in a significant increase of FVIII activity in plasma level as compared to administration of FVIII alone or FVIII+dextran sulfate. The increase for co-administration of heparin was particularly strong.

TABLE 3

FVIII activity in % of the FVIII activity in normal human plasma

| Time-point (h) | rFVIII 400 IU/kg s.c. | rFVIII 400 IU/kg / unfractionated Heparin 5 U/mL (40 U/kg) s.c. | rFVIII 400 IU/kg / Dextransulfate 400 µg/ml s.c. | rFVIII 400 IU/kg / Fragmin 5 U/mL (40 U/kg) s.c. |
|---|---|---|---|---|
| 0.5 | 1.02 ± 0.85 | 2.90 ± 2.70 | 0 ± 0 | 3.41 ± 0.61 |
| 2 | 13.04 ± 3.90 | 15.16 ± 4.12 | 0.98 ± 1.49 | 10.65 ± 6.38 |
| 5 | 1.15 ± 1.28 | 26.66 ± 5.74 | 2.57 ± 2.67 | 15.19 ± 7.12 |
| 8 | 2.32 ± 2.27 | 15.56 ± 4.22 | 0.64 ± 0.64 | 21.13 ± 8.92 |
| 16 | 4.82 ± 2.35 | 12.08 ± 2.35 | 0.84 ± 1.26 | 13.19 ± 3.58 |
| 24 | 9.72 ± 8.09 | 14.10 ± 3.76 | 0.85 ± 0.89 | 10.21 ± 3.26 |
| 32 | 2.48 ± 2.20 | 10.84 ± 5.31 | 0.92 ± 1.30 | 5.23 ± 2.83 |
| 48 | 1.15 ± 1.72 | 7.02 ± 1.24 | 1.47 ± 1.14 | 4.71 ± 1.74 |
| AUC 0-48 h (h x % of the norm SHP) | 202.0 | 598.4 | 50.0 | 475.9 |

The peak values are shaded in grey.

| Time-point (h) | rFVIII 400 IU/kg/ Fondaparinux (10 µg/ml) s.c. | rFVIII 400 IU/kg/ N-acetyl de-O-sulfated Heparin (10 µg/ml) s.c. | rFVIII 400 IU/kg/ Chondroitin sulfate (10 µg/mL) s.c. |
|---|---|---|---|
| 0.5 | 7.21 ± 6.77 | 8.24 ± 11.87 | 1.98 ± 4.12 |
| 2 | 20.81 ± 11.42 | 23.37 ± 8.39 | 16.83 ± 7.22 |
| 5 | 13.01 ± 8.96 | 16.75 ± 5.08 | 11.59 ± 5.28 |
| 8 | 18.03 ± 4.70 | 28.73 ± 9.39 | 22.59 ± 7.10 |
| 16 | 8.79 ± 5.67 | 7.69 ± 5.31 | 3.86 ± 2.76 |
| 24 | 9.61 ± 5.66 | 10.49 ± 2.12 | 8.95 ± 2.25 |
| 32 | 3.81 ± 2.13 | 4.11 ± 1.99 | 2.83 ± 1.67 |
| 48 | 6.55 ± 2.93 | 4.73 ± 1.37 | 7.11 ± 2.86 |
| AUC (h x % of the norm SHP)) | 435.7 | 499.6 | 391.7 |

The peak values are shaded in grey.

The invention claimed is:

1. A method of treatment or prophylaxis for a bleeding disorder, the method comprising:
    administering to a patient in need thereof a first pharmaceutical composition comprising Factor VIII by a non-intravenous route, wherein the Factor VIII is administered at a dose ranging from about 50 IU/kg body weight to about 800 IU/kg body weight; and
    administering a second pharmaceutical composition comprising a sulfated glycosaminoglycan by a non-intravenous route, wherein the sulfated glycosaminoglycan is administered at a dose ranging from about 0.001 to about 100 mg per mL product applied, wherein the administered dosage of the Factor VIII and the sulfated glycosaminoglycan are sufficient to maintain a blood plasma level in the patient of more than 2% of the normal plasma level of Factor VIII in a healthy subject during a period from 1 hour after administration to 48 hours after administration, wherein the non-intravenous route is selected from the group consisting of subcutaneous, intramuscular, intraperitoneal, intradermal or transdermal administration,
    thereby providing treatment or prophylaxis for the bleeding disorder.

2. The method of claim 1, wherein the sulfated glycosaminoglycan is heparin.

3. The method of claim 2, wherein the heparin is unfractionated heparin.

4. The method of claim 3, wherein the average molecular weight of the unfractionated heparin ranges from about 8 kDa to about 30 kDa.

5. The method of claim 1, wherein the Factor VIII is in a complex with von Willebrand Factor.

6. The method of claim 1, wherein the method comprises simultaneously administering the first pharmaceutical composition and the second pharmaceutical composition.

7. The method of claim 1, wherein the method comprises sequentially administering the first pharmaceutical composition and the second pharmaceutical composition.

8. The method of claim 1, wherein the non-intravenous administration is subcutaneous.

9. The method of claim 1, wherein the bleeding disorder is hemophilia A.

10. A method for increasing the bioavailability of an administered Factor VIII composition, the method comprising:
- administering a first pharmaceutical composition comprising Factor VIII by a non-intravenous route, wherein the Factor VIII is administered at a dose ranging from about 50 IU/kg body weight to about 800 IU/kg body weight; and
- administering a second pharmaceutical composition comprising a sulfated glycosaminoglycan by a non-intravenous route, wherein the sulfated glycosaminoglycan is administered at a dose ranging from about 0.001 to about 100 mg per mL product applied,
- wherein the first pharmaceutical composition and the second pharmaceutical composition are administered at a dose that results in at least about a 20% increase in the bioavailability of Factor VIII relative to the bioavailability when Factor VIII is administered without the second pharmaceutical composition and wherein the non-intravenous route is selected from the group consisting of subcutaneous, intramuscular, intraperitoneal, intradermal or transdermal administration.

11. The method of claim 10, wherein the sulfated glycosaminoglycan is heparin.

12. The method of claim 11, wherein the heparin is unfractionated heparin.

13. The method of claim 12, wherein the average molecular weight of the unfractionated heparin ranges from about 8 kDa to about 30 kDa.

14. The method of claim 10, wherein the non-intravenous administration is subcutaneous, transdermal or intramuscular administration.

15. The method of claim 1, wherein the sulfated glycosaminoglycan is chosen from heparin and chondroitin.

16. The method of claim 10, wherein the sulfated glycosaminoglycan is chosen from heparin and chondroitin.

17. The method of claim 1, wherein the first and second pharmaceutical compositions are administered subcutaneously.

18. The method of claim 10, wherein the first and second pharmaceutical compositions are administered subcutaneously.

* * * * *

SEQUENCE LISTING

```
<160> NUMBER OF SEQ ID NOS: 2

<210> SEQ ID NO 1
<211> LENGTH: 6996
<212> TYPE: DNA
<213> ORGANISM: homo sapiens
<220> FEATURE:
<221> NAME/KEY: CDS
<222> LOCATION: (1)..(6996)

<400> SEQUENCE: 1 gcc acc aga aga tac tac ctg ggt gca gtg gaa ctg tca tgg gac tat      48
Ala Thr Arg Arg Tyr Tyr Leu Gly Ala Val Glu Leu Ser Trp Asp Tyr
1               5                   10                  15
```

| | | |
|---|---|---|
| atg caa agt gat ctc ggt gag ctg cct gtg gac gca aga ttt cct cct<br>Met Gln Ser Asp Leu Gly Glu Leu Pro Val Asp Ala Arg Phe Pro Pro<br>          20                  25                  30 | | 96 |
| aga gtg cca aaa tct ttt cca ttc aac acc tca gtc gtg tac aaa aag<br>Arg Val Pro Lys Ser Phe Pro Phe Asn Thr Ser Val Val Tyr Lys Lys<br>          35                  40                  45 | | 144 |
| act ctg ttt gta gaa ttc acg gat cac ctt ttc aac atc gct aag cca<br>Thr Leu Phe Val Glu Phe Thr Asp His Leu Phe Asn Ile Ala Lys Pro<br>50                  55                  60 | | 192 |
| agg cca ccc tgg atg ggt ctg cta ggt cct acc atc cag gct gag gtt<br>Arg Pro Pro Trp Met Gly Leu Leu Gly Pro Thr Ile Gln Ala Glu Val<br>65                  70                  75                  80 | | 240 |
| tat gat aca gtg gtc att aca ctt aag aac atg gct tcc cat cct gtc<br>Tyr Asp Thr Val Val Ile Thr Leu Lys Asn Met Ala Ser His Pro Val<br>                  85                  90                  95 | | 288 |
| agt ctt cat gct gtt ggt gta tcc tac tgg aaa gct tct gag gga gct<br>Ser Leu His Ala Val Gly Val Ser Tyr Trp Lys Ala Ser Glu Gly Ala<br>                  100                105                110 | | 336 |
| gaa tat gat gat cag acc agt caa agg gag aaa gaa gat gat aaa gtc<br>Glu Tyr Asp Asp Gln Thr Ser Gln Arg Glu Lys Glu Asp Asp Lys Val<br>                115                120                125 | | 384 |
| ttc cct ggt gga agc cat aca tat gtc tgg cag gtc ctg aaa gag aat<br>Phe Pro Gly Gly Ser His Thr Tyr Val Trp Gln Val Leu Lys Glu Asn<br>130                  135                140 | | 432 |
| ggt cca atg gcc tct gac cca ctg tgc ctt acc tac tca tat ctt tct<br>Gly Pro Met Ala Ser Asp Pro Leu Cys Leu Thr Tyr Ser Tyr Leu Ser<br>145                  150                155                160 | | 480 |
| cat gtg gac ctg gta aaa gac ttg aat tca ggc ctc att gga gcc cta<br>His Val Asp Leu Val Lys Asp Leu Asn Ser Gly Leu Ile Gly Ala Leu<br>                  165                170                175 | | 528 |
| cta gta tgt aga gaa ggg agt ctg gcc aag gaa aag aca cag acc ttg<br>Leu Val Cys Arg Glu Gly Ser Leu Ala Lys Glu Lys Thr Gln Thr Leu<br>                180                185                190 | | 576 |
| cac aaa ttt ata cta ctt ttt gct gta ttt gat gaa ggg aaa agt tgg<br>His Lys Phe Ile Leu Leu Phe Ala Val Phe Asp Glu Gly Lys Ser Trp<br>              195                200                205 | | 624 |
| cac tca gaa aca aag aac tcc ttg atg cag gat agg gat gct gca tct<br>His Ser Glu Thr Lys Asn Ser Leu Met Gln Asp Arg Asp Ala Ala Ser<br>210                  215                220 | | 672 |
| gct cgg gcc tgg cct aaa atg cac aca gtc aat ggt tat gta aac agg<br>Ala Arg Ala Trp Pro Lys Met His Thr Val Asn Gly Tyr Val Asn Arg<br>225                  230                235                240 | | 720 |
| tct ctg cca ggt ctg att gga tgc cac agg aaa tca gtc tat tgg cat<br>Ser Leu Pro Gly Leu Ile Gly Cys His Arg Lys Ser Val Tyr Trp His<br>                245                250                255 | | 768 |
| gtg att gga atg ggc acc act cct gaa gtg cac tca ata ttc ctc gaa<br>Val Ile Gly Met Gly Thr Thr Pro Glu Val His Ser Ile Phe Leu Glu<br>                  260                265                270 | | 816 |
| ggt cac aca ttt ctt gtg agg aac cat cgc cag gcg tcc ttg gaa atc<br>Gly His Thr Phe Leu Val Arg Asn His Arg Gln Ala Ser Leu Glu Ile<br>              275                280                285 | | 864 |
| tcg cca ata act ttc ctt act gct caa aca ctc ttg atg gac ctt gga<br>Ser Pro Ile Thr Phe Leu Thr Ala Gln Thr Leu Leu Met Asp Leu Gly<br>290                  295                300 | | 912 |
| cag ttt cta ctg ttt tgt cat atc tct tcc cac caa cat gat ggc atg<br>Gln Phe Leu Leu Phe Cys His Ile Ser Ser His Gln His Asp Gly Met<br>305                  310                315                320 | | 960 |
| gaa gct tat gtc aaa gta gac agc tgt cca gag gaa ccc caa cta cga<br>Glu Ala Tyr Val Lys Val Asp Ser Cys Pro Glu Glu Pro Gln Leu Arg<br>              325                330                335 | | 1008 |

```
atg aaa aat aat gaa gaa gcg gaa gac tat gat gat gat ctt act gat    1056
Met Lys Asn Asn Glu Glu Ala Glu Asp Tyr Asp Asp Asp Leu Thr Asp
        340                 345                 350 tct gaa atg gat gtg gtc agg ttt gat gat gac aac tct cct tcc ttt    1104
Ser Glu Met Asp Val Val Arg Phe Asp Asp Asp Asn Ser Pro Ser Phe
            355                 360                 365 atc caa att cgc tca gtt gcc aag aag cat cct aaa act tgg gta cat    1152
Ile Gln Ile Arg Ser Val Ala Lys Lys His Pro Lys Thr Trp Val His
370                 375                 380 tac att gct gct gaa gag gag gac tgg gac tat gct ccc tta gtc ctc    1200
Tyr Ile Ala Ala Glu Glu Glu Asp Trp Asp Tyr Ala Pro Leu Val Leu
385                 390                 395                 400 gcc ccc gat gac aga agt tat aaa agt caa tat ttg aac aat ggc cct    1248
Ala Pro Asp Asp Arg Ser Tyr Lys Ser Gln Tyr Leu Asn Asn Gly Pro
            405                 410                 415 cag cgg att ggt agg aag tac aaa aaa gtc cga ttt atg gca tac aca    1296
Gln Arg Ile Gly Arg Lys Tyr Lys Lys Val Arg Phe Met Ala Tyr Thr
            420                 425                 430 gat gaa acc ttt aag act cgt gaa gct att cag cat gaa tca gga atc    1344
Asp Glu Thr Phe Lys Thr Arg Glu Ala Ile Gln His Glu Ser Gly Ile
            435                 440                 445 ttg gga cct tta ctt tat ggg gaa gtt gga gac aca ctg ttg att ata    1392
Leu Gly Pro Leu Leu Tyr Gly Glu Val Gly Asp Thr Leu Leu Ile Ile
450                 455                 460 ttt aag aat caa gca agc aga cca tat aac atc tac cct cac gga atc    1440
Phe Lys Asn Gln Ala Ser Arg Pro Tyr Asn Ile Tyr Pro His Gly Ile
465                 470                 475                 480 act gat gtc cgt cct ttg tat tca agg aga tta cca aaa ggt gta aaa    1488
Thr Asp Val Arg Pro Leu Tyr Ser Arg Arg Leu Pro Lys Gly Val Lys
            485                 490                 495 cat ttg aag gat ttt cca att ctg cca gga gaa ata ttc aaa tat aaa    1536
His Leu Lys Asp Phe Pro Ile Leu Pro Gly Glu Ile Phe Lys Tyr Lys
            500                 505                 510 tgg aca gtg act gta gaa gat ggg cca act aaa tca gat cct cgg tgc    1584
Trp Thr Val Thr Val Glu Asp Gly Pro Thr Lys Ser Asp Pro Arg Cys
            515                 520                 525 ctg acc cgc tat tac tct agt ttc gtt aat atg gag aga gat cta gct    1632
Leu Thr Arg Tyr Tyr Ser Ser Phe Val Asn Met Glu Arg Asp Leu Ala
530                 535                 540 tca gga ctc att ggc cct ctc ctc atc tgc tac aaa gaa tct gta gat    1680
Ser Gly Leu Ile Gly Pro Leu Leu Ile Cys Tyr Lys Glu Ser Val Asp
545                 550                 555                 560 caa aga gga aac cag ata atg tca gac aag agg aat gtc atc ctg ttt    1728
Gln Arg Gly Asn Gln Ile Met Ser Asp Lys Arg Asn Val Ile Leu Phe
            565                 570                 575 tct gta ttt gat gag aac cga agc tgg tac ctc aca gag aat ata caa    1776
Ser Val Phe Asp Glu Asn Arg Ser Trp Tyr Leu Thr Glu Asn Ile Gln
            580                 585                 590 cgc ttt ctc ccc aat cca gct gga gtg cag ctt gag gat cca gag ttc    1824
Arg Phe Leu Pro Asn Pro Ala Gly Val Gln Leu Glu Asp Pro Glu Phe
            595                 600                 605 caa gcc tcc aac atc atg cac agc atc aat ggc tat gtt ttt gat agt    1872
Gln Ala Ser Asn Ile Met His Ser Ile Asn Gly Tyr Val Phe Asp Ser
            610                 615                 620 ttg cag ttg tca gtt tgt ttg cat gag gtg gca tac tgg tac att cta    1920
Leu Gln Leu Ser Val Cys Leu His Glu Val Ala Tyr Trp Tyr Ile Leu
625                 630                 635                 640
```

```
agc att gga gca cag act gac ttc ctt tct gtc ttc ttc tct gga tat    1968
Ser Ile Gly Ala Gln Thr Asp Phe Leu Ser Val Phe Phe Ser Gly Tyr
            645                 650                 655 acc ttc aaa cac aaa atg gtc tat gaa gac aca ctc acc cta ttc cca    2016
Thr Phe Lys His Lys Met Val Tyr Glu Asp Thr Leu Thr Leu Phe Pro
        660                 665                 670 ttc tca gga gaa act gtc ttc atg tcg atg gaa aac cca ggt cta tgg    2064
Phe Ser Gly Glu Thr Val Phe Met Ser Met Glu Asn Pro Gly Leu Trp
    675                 680                 685 att ctg ggg tgc cac aac tca gac ttt cgg aac aga ggc atg acc gcc    2112
Ile Leu Gly Cys His Asn Ser Asp Phe Arg Asn Arg Gly Met Thr Ala
690                 695                 700 tta ctg aag gtt tct agt tgt gac aag aac act ggt gat tat tac gag    2160
Leu Leu Lys Val Ser Ser Cys Asp Lys Asn Thr Gly Asp Tyr Tyr Glu
705                 710                 715                 720 gac agt tat gaa gat att tca gca tac ttg ctg agt aaa aac aat gcc    2208
Asp Ser Tyr Glu Asp Ile Ser Ala Tyr Leu Leu Ser Lys Asn Asn Ala
                725                 730                 735 att gaa cca aga agc ttc tcc cag aat tca aga cac cgt agc act agg    2256
Ile Glu Pro Arg Ser Phe Ser Gln Asn Ser Arg His Arg Ser Thr Arg
            740                 745                 750 caa aag caa ttt aat gcc acc aca att cca gaa aat gac ata gag aag    2304
Gln Lys Gln Phe Asn Ala Thr Thr Ile Pro Glu Asn Asp Ile Glu Lys
        755                 760                 765 act gac cct tgg ttt gca cac aga aca cct atg cct aaa ata caa aat    2352
Thr Asp Pro Trp Phe Ala His Arg Thr Pro Met Pro Lys Ile Gln Asn
    770                 775                 780 gtc tcc tct agt gat ttg ttg atg ctc ttg cga cag agt cct act cca    2400
Val Ser Ser Ser Asp Leu Leu Met Leu Leu Arg Gln Ser Pro Thr Pro
785                 790                 795                 800 cat ggg cta tcc tta tct gat ctc caa gaa gcc aaa tat gag act ttt    2448
His Gly Leu Ser Leu Ser Asp Leu Gln Glu Ala Lys Tyr Glu Thr Phe
                805                 810                 815 tct gat gat cca tca cct gga gca ata gac agt aat aac agc ctg tct    2496
Ser Asp Asp Pro Ser Pro Gly Ala Ile Asp Ser Asn Asn Ser Leu Ser
            820                 825                 830 gaa atg aca cac ttc agg cca cag ctc cat cac agt ggg gac atg gta    2544
Glu Met Thr His Phe Arg Pro Gln Leu His His Ser Gly Asp Met Val
        835                 840                 845 ttt acc cct gag tca ggc ctc caa tta aga tta aat gag aaa ctg ggg    2592
Phe Thr Pro Glu Ser Gly Leu Gln Leu Arg Leu Asn Glu Lys Leu Gly
    850                 855                 860 aca act gca gca aca gag ttg aag aaa ctt gat ttc aaa gtt tct agt    2640
Thr Thr Ala Ala Thr Glu Leu Lys Lys Leu Asp Phe Lys Val Ser Ser
865                 870                 875                 880 aca tca aat aat ctg att tca aca att cca tca gac aat ttg gca gca    2688
Thr Ser Asn Asn Leu Ile Ser Thr Ile Pro Ser Asp Asn Leu Ala Ala
                885                 890                 895 ggt act gat aat aca agt tcc tta gga ccc cca agt atg cca gtt cat    2736
Gly Thr Asp Asn Thr Ser Ser Leu Gly Pro Pro Ser Met Pro Val His
            900                 905                 910 tat gat agt caa tta gat acc act cta ttt ggc aaa aag tca tct ccc    2784
Tyr Asp Ser Gln Leu Asp Thr Thr Leu Phe Gly Lys Lys Ser Ser Pro
        915                 920                 925 ctt act gag tct ggt gga cct ctg agc ttg agt gaa gaa aat aat gat    2832
Leu Thr Glu Ser Gly Gly Pro Leu Ser Leu Ser Glu Glu Asn Asn Asp
    930                 935                 940 tca aag ttg tta gaa tca ggt tta atg aat agc caa gaa agt tca tgg    2880
Ser Lys Leu Leu Glu Ser Gly Leu Met Asn Ser Gln Glu Ser Ser Trp
945                 950                 955                 960
```

-continued

```
gga aaa aat gta tcg tca aca gag agt ggt agg tta ttt aaa ggg aaa       2928
Gly Lys Asn Val Ser Ser Thr Glu Ser Gly Arg Leu Phe Lys Gly Lys
            965                 970                 975 aga gct cat gga cct gct ttg ttg act aaa gat aat gcc tta ttc aaa       2976
Arg Ala His Gly Pro Ala Leu Leu Thr Lys Asp Asn Ala Leu Phe Lys
            980                 985                 990 gtt agc atc tct ttg tta aag aca aac aaa act tcc aat aat tca gca       3024
Val Ser Ile Ser Leu Leu Lys Thr Asn Lys Thr Ser Asn Asn Ser Ala
            995                 1000                1005 act aat aga aag act cac att gat ggc cca tca tta tta att gag           3069
Thr Asn Arg Lys Thr His Ile Asp Gly Pro Ser Leu Leu Ile Glu
            1010                1015                1020 aat agt cca tca gtc tgg caa aat ata tta gaa agt gac act gag           3114
Asn Ser Pro Ser Val Trp Gln Asn Ile Leu Glu Ser Asp Thr Glu
            1025                1030                1035 ttt aaa aaa gtg aca cct ttg att cat gac aga atg ctt atg gac           3159
Phe Lys Lys Val Thr Pro Leu Ile His Asp Arg Met Leu Met Asp
            1040                1045                1050 aaa aat gct aca gct ttg agg cta aat cat atg tca aat aaa act           3204
Lys Asn Ala Thr Ala Leu Arg Leu Asn His Met Ser Asn Lys Thr
            1055                1060                1065 act tca tca aaa aac atg gaa atg gtc caa cag aaa aaa gag ggc           3249
Thr Ser Ser Lys Asn Met Glu Met Val Gln Gln Lys Lys Glu Gly
            1070                1075                1080 ccc att cca cca gat gca caa aat cca gat atg tcg ttc ttt aag           3294
Pro Ile Pro Pro Asp Ala Gln Asn Pro Asp Met Ser Phe Phe Lys
            1085                1090                1095 atg cta ttc ttg cca gaa tca gca agg tgg ata caa agg act cat           3339
Met Leu Phe Leu Pro Glu Ser Ala Arg Trp Ile Gln Arg Thr His
            1100                1105                1110 gga aag aac tct ctg aac tct ggg caa ggc ccc agt cca aag caa           3384
Gly Lys Asn Ser Leu Asn Ser Gly Gln Gly Pro Ser Pro Lys Gln
            1115                1120                1125 tta gta tcc tta gga cca gaa aaa tct gtg gaa ggt cag aat ttc           3429
Leu Val Ser Leu Gly Pro Glu Lys Ser Val Glu Gly Gln Asn Phe
            1130                1135                1140 ttg tct gag aaa aac aaa gtg gta gta gga aag ggt gaa ttt aca           3474
Leu Ser Glu Lys Asn Lys Val Val Val Gly Lys Gly Glu Phe Thr
            1145                1150                1155 aag gac gta gga ctc aaa gag atg gtt ttt cca agc agc aga aac           3519
Lys Asp Val Gly Leu Lys Glu Met Val Phe Pro Ser Ser Arg Asn
            1160                1165                1170 cta ttt ctt act aac ttg gat aat tta cat gaa aat aat aca cac           3564
Leu Phe Leu Thr Asn Leu Asp Asn Leu His Glu Asn Asn Thr His
            1175                1180                1185 aat caa gaa aaa aaa att cag gaa gaa ata gaa aag aag gaa aca           3609
Asn Gln Glu Lys Lys Ile Gln Glu Glu Ile Glu Lys Lys Glu Thr
            1190                1195                1200 tta atc caa gag aat gta gtt ttg cct cag ata cat aca gtg act           3654
Leu Ile Gln Glu Asn Val Val Leu Pro Gln Ile His Thr Val Thr
            1205                1210                1215 ggc act aag aat ttc atg aag aac ctt ttc tta ctg agc act agg           3699
Gly Thr Lys Asn Phe Met Lys Asn Leu Phe Leu Leu Ser Thr Arg
            1220                1225                1230 caa aat gta gaa ggt tca tat gac ggg gca tat gct cca gta ctt           3744
Gln Asn Val Glu Gly Ser Tyr Asp Gly Ala Tyr Ala Pro Val Leu
            1235                1240                1245
```

-continued

| | | | | | | | | | | | | | | | |
|---|---|---|---|---|---|---|---|---|---|---|---|---|---|---|---|
| caa | gat | ttt | agg | tca | tta | aat | gat | tca | aca | aat | aga | aca | aag | aaa | 3789 |
| Gln | Asp | Phe | Arg | Ser | Leu | Asn | Asp | Ser | Thr | Asn | Arg | Thr | Lys | Lys | |
| 1250 | | | | 1255 | | | | | 1260 | | | | | | |
| cac | aca | gct | cat | ttc | tca | aaa | aaa | ggg | gag | gaa | gaa | aac | ttg | gaa | 3834 |
| His | Thr | Ala | His | Phe | Ser | Lys | Lys | Gly | Glu | Glu | Glu | Asn | Leu | Glu | |
| 1265 | | | | 1270 | | | | | 1275 | | | | | | |
| ggc | ttg | gga | aat | caa | acc | aag | caa | att | gta | gag | aaa | tat | gca | tgc | 3879 |
| Gly | Leu | Gly | Asn | Gln | Thr | Lys | Gln | Ile | Val | Glu | Lys | Tyr | Ala | Cys | |
| 1280 | | | | 1285 | | | | | 1290 | | | | | | |
| acc | aca | agg | ata | tct | cct | aat | aca | agc | cag | cag | aat | ttt | gtc | acg | 3924 |
| Thr | Thr | Arg | Ile | Ser | Pro | Asn | Thr | Ser | Gln | Gln | Asn | Phe | Val | Thr | |
| 1295 | | | | 1300 | | | | | 1305 | | | | | | |
| caa | cgt | agt | aag | aga | gct | ttg | aaa | caa | ttc | aga | ctc | cca | cta | gaa | 3969 |
| Gln | Arg | Ser | Lys | Arg | Ala | Leu | Lys | Gln | Phe | Arg | Leu | Pro | Leu | Glu | |
| 1310 | | | | 1315 | | | | | 1320 | | | | | | |
| gaa | aca | gaa | ctt | gaa | aaa | agg | ata | att | gtg | gat | gac | acc | tca | acc | 4014 |
| Glu | Thr | Glu | Leu | Glu | Lys | Arg | Ile | Ile | Val | Asp | Asp | Thr | Ser | Thr | |
| 1325 | | | | 1330 | | | | | 1335 | | | | | | |
| cag | tgg | tcc | aaa | aac | atg | aaa | cat | ttg | acc | ccg | agc | acc | ctc | aca | 4059 |
| Gln | Trp | Ser | Lys | Asn | Met | Lys | His | Leu | Thr | Pro | Ser | Thr | Leu | Thr | |
| 1340 | | | | 1345 | | | | | 1350 | | | | | | |
| cag | ata | gac | tac | aat | gag | aag | gag | aaa | ggg | gcc | att | act | cag | tct | 4104 |
| Gln | Ile | Asp | Tyr | Asn | Glu | Lys | Glu | Lys | Gly | Ala | Ile | Thr | Gln | Ser | |
| 1355 | | | | 1360 | | | | | 1365 | | | | | | |
| ccc | tta | tca | gat | tgc | ctt | acg | agg | agt | cat | agc | atc | cct | caa | gca | 4149 |
| Pro | Leu | Ser | Asp | Cys | Leu | Thr | Arg | Ser | His | Ser | Ile | Pro | Gln | Ala | |
| 1370 | | | | 1375 | | | | | 1380 | | | | | | |
| aat | aga | tct | cca | tta | ccc | att | gca | aag | gta | tca | tca | ttt | cca | tct | 4194 |
| Asn | Arg | Ser | Pro | Leu | Pro | Ile | Ala | Lys | Val | Ser | Ser | Phe | Pro | Ser | |
| 1385 | | | | 1390 | | | | | 1395 | | | | | | |
| att | aga | cct | ata | tat | ctg | acc | agg | gtc | cta | ttc | caa | gac | aac | tct | 4239 |
| Ile | Arg | Pro | Ile | Tyr | Leu | Thr | Arg | Val | Leu | Phe | Gln | Asp | Asn | Ser | |
| 1400 | | | | 1405 | | | | | 1410 | | | | | | |
| tct | cat | ctt | cca | gca | gca | tct | tat | aga | aag | aaa | gat | tct | ggg | gtc | 4284 |
| Ser | His | Leu | Pro | Ala | Ala | Ser | Tyr | Arg | Lys | Lys | Asp | Ser | Gly | Val | |
| 1415 | | | | 1420 | | | | | 1425 | | | | | | |
| caa | gaa | agc | agt | cat | ttc | tta | caa | gga | gcc | aaa | aaa | aat | aac | ctt | 4329 |
| Gln | Glu | Ser | Ser | His | Phe | Leu | Gln | Gly | Ala | Lys | Lys | Asn | Asn | Leu | |
| 1430 | | | | 1435 | | | | | 1440 | | | | | | |
| tct | tta | gcc | att | cta | acc | ttg | gag | atg | act | ggt | gat | caa | aga | gag | 4374 |
| Ser | Leu | Ala | Ile | Leu | Thr | Leu | Glu | Met | Thr | Gly | Asp | Gln | Arg | Glu | |
| 1445 | | | | 1450 | | | | | 1455 | | | | | | |
| gtt | ggc | tcc | ctg | ggg | aca | agt | gcc | aca | aat | tca | gtc | aca | tac | aag | 4419 |
| Val | Gly | Ser | Leu | Gly | Thr | Ser | Ala | Thr | Asn | Ser | Val | Thr | Tyr | Lys | |
| 1460 | | | | 1465 | | | | | 1470 | | | | | | |
| aaa | gtt | gag | aac | act | gtt | ctc | ccg | aaa | cca | gac | ttg | ccc | aaa | aca | 4464 |
| Lys | Val | Glu | Asn | Thr | Val | Leu | Pro | Lys | Pro | Asp | Leu | Pro | Lys | Thr | |
| 1475 | | | | 1480 | | | | | 1485 | | | | | | |
| tct | ggc | aaa | gtt | gaa | ttg | ctt | cca | aaa | gtt | cac | att | tat | cag | aag | 4509 |
| Ser | Gly | Lys | Val | Glu | Leu | Leu | Pro | Lys | Val | His | Ile | Tyr | Gln | Lys | |
| 1490 | | | | 1495 | | | | | 1500 | | | | | | |
| gac | cta | ttc | cct | acg | gaa | act | agc | aat | ggg | tct | cct | ggc | cat | ctg | 4554 |
| Asp | Leu | Phe | Pro | Thr | Glu | Thr | Ser | Asn | Gly | Ser | Pro | Gly | His | Leu | |
| 1505 | | | | 1510 | | | | | 1515 | | | | | | |
| gat | ctc | gtg | gaa | ggg | agc | ctt | ctt | cag | gga | aca | gag | gga | gcg | att | 4599 |
| Asp | Leu | Val | Glu | Gly | Ser | Leu | Leu | Gln | Gly | Thr | Glu | Gly | Ala | Ile | |
| 1520 | | | | 1525 | | | | | 1530 | | | | | | |
| aag | tgg | aat | gaa | gca | aac | aga | cct | gga | aaa | gtt | ccc | ttt | ctg | aga | 4644 |
| Lys | Trp | Asn | Glu | Ala | Asn | Arg | Pro | Gly | Lys | Val | Pro | Phe | Leu | Arg | |
| 1535 | | | | 1540 | | | | | 1545 | | | | | | |

```
gta gca aca gaa agc tct gca aag act ccc tcc aag cta ttg gat      4689
Val Ala Thr Glu Ser Ser Ala Lys Thr Pro Ser Lys Leu Leu Asp
    1550            1555                1560 cct ctt gct tgg gat aac cac tat ggt act cag ata cca aaa gaa      4734
Pro Leu Ala Trp Asp Asn His Tyr Gly Thr Gln Ile Pro Lys Glu
    1565            1570                1575 gag tgg aaa tcc caa gag aag tca cca gaa aaa aca gct ttt aag      4779
Glu Trp Lys Ser Gln Glu Lys Ser Pro Glu Lys Thr Ala Phe Lys
    1580            1585                1590 aaa aag gat acc att ttg tcc ctg aac gct tgt gaa agc aat cat      4824
Lys Lys Asp Thr Ile Leu Ser Leu Asn Ala Cys Glu Ser Asn His
    1595            1600                1605 gca ata gca gca ata aat gag gga caa aat aag ccc gaa ata gaa      4869
Ala Ile Ala Ala Ile Asn Glu Gly Gln Asn Lys Pro Glu Ile Glu
    1610            1615                1620 gtc acc tgg gca aag caa ggt agg act gaa agg ctg tgc tct caa      4914
Val Thr Trp Ala Lys Gln Gly Arg Thr Glu Arg Leu Cys Ser Gln
    1625            1630                1635 aac cca cca gtc ttg aaa cgc cat caa cgg gaa ata act cgt act      4959
Asn Pro Pro Val Leu Lys Arg His Gln Arg Glu Ile Thr Arg Thr
    1640            1645                1650 act ctt cag tca gat caa gag gaa att gac tat gat gat acc ata      5004
Thr Leu Gln Ser Asp Gln Glu Glu Ile Asp Tyr Asp Asp Thr Ile
    1655            1660                1665 tca gtt gaa atg aag aag gaa gat ttt gac att tat gat gag gat      5049
Ser Val Glu Met Lys Lys Glu Asp Phe Asp Ile Tyr Asp Glu Asp
    1670            1675                1680 gaa aat cag agc ccc cgc agc ttt caa aag aaa aca cga cac tat      5094
Glu Asn Gln Ser Pro Arg Ser Phe Gln Lys Lys Thr Arg His Tyr
    1685            1690                1695 ttt att gct gca gtg gag agg ctc tgg gat tat ggg atg agt agc      5139
Phe Ile Ala Ala Val Glu Arg Leu Trp Asp Tyr Gly Met Ser Ser
    1700            1705                1710 tcc cca cat gtt cta aga aac agg gct cag agt ggc agt gtc cct      5184
Ser Pro His Val Leu Arg Asn Arg Ala Gln Ser Gly Ser Val Pro
    1715            1720                1725 cag ttc aag aaa gtt gtt ttc cag gaa ttt act gat ggc tcc ttt      5229
Gln Phe Lys Lys Val Val Phe Gln Glu Phe Thr Asp Gly Ser Phe
    1730            1735                1740 act cag ccc tta tac cgt gga gaa cta aat gaa cat ttg gga ctc      5274
Thr Gln Pro Leu Tyr Arg Gly Glu Leu Asn Glu His Leu Gly Leu
    1745            1750                1755 ctg ggg cca tat ata aga gca gaa gtt gaa gat aat atc atg gta      5319
Leu Gly Pro Tyr Ile Arg Ala Glu Val Glu Asp Asn Ile Met Val
    1760            1765                1770 act ttc aga aat cag gcc tct cgt ccc tat tcc ttc tat tct agc      5364
Thr Phe Arg Asn Gln Ala Ser Arg Pro Tyr Ser Phe Tyr Ser Ser
    1775            1780                1785 ctt att tct tat gag gaa gat cag agg caa gga gca gaa cct aga      5409
Leu Ile Ser Tyr Glu Glu Asp Gln Arg Gln Gly Ala Glu Pro Arg
    1790            1795                1800 aaa aac ttt gtc aag cct aat gaa acc aaa act tac ttt tgg aaa      5454
Lys Asn Phe Val Lys Pro Asn Glu Thr Lys Thr Tyr Phe Trp Lys
    1805            1810                1815 gtg caa cat cat atg gca ccc act aaa gat gag ttt gac tgc aaa      5499
Val Gln His His Met Ala Pro Thr Lys Asp Glu Phe Asp Cys Lys
    1820            1825                1830
```

-continued

| | | |
|---|---|---|
| gcc tgg gct tat ttc tct gat gtt gac ctg gaa aaa gat gtg cac<br>Ala Trp Ala Tyr Phe Ser Asp Val Asp Leu Glu Lys Asp Val His<br>1835                          1840                        1845 | 5544 | |
| tca ggc ctg att gga ccc ctt ctg gtc tgc cac act aac aca ctg<br>Ser Gly Leu Ile Gly Pro Leu Leu Val Cys His Thr Asn Thr Leu<br>1850                          1855                        1860 | 5589 | |
| aac cct gct cat ggg aga caa gtg aca gta cag gaa ttt gct ctg<br>Asn Pro Ala His Gly Arg Gln Val Thr Val Gln Glu Phe Ala Leu<br>1865                          1870                        1875 | 5634 | |
| ttt ttc acc atc ttt gat gag acc aaa agc tgg tac ttc act gaa<br>Phe Phe Thr Ile Phe Asp Glu Thr Lys Ser Trp Tyr Phe Thr Glu<br>1880                          1885                        1890 | 5679 | |
| aat atg gaa aga aac tgc agg gct ccc tgc aat atc cag atg gaa<br>Asn Met Glu Arg Asn Cys Arg Ala Pro Cys Asn Ile Gln Met Glu<br>1895                          1900                        1905 | 5724 | |
| gat ccc act ttt aaa gag aat tat cgc ttc cat gca atc aat ggc<br>Asp Pro Thr Phe Lys Glu Asn Tyr Arg Phe His Ala Ile Asn Gly<br>1910                          1915                        1920 | 5769 | |
| tac ata atg gat aca cta cct ggc tta gta atg gct cag gat caa<br>Tyr Ile Met Asp Thr Leu Pro Gly Leu Val Met Ala Gln Asp Gln<br>1925                          1930                        1935 | 5814 | |
| agg att cga tgg tat ctg ctc agc atg ggc agc aat gaa aac atc<br>Arg Ile Arg Trp Tyr Leu Leu Ser Met Gly Ser Asn Glu Asn Ile<br>1940                          1945                        1950 | 5859 | |
| cat tct att cat ttc agt gga cat gtg ttc act gta cga aaa aaa<br>His Ser Ile His Phe Ser Gly His Val Phe Thr Val Arg Lys Lys<br>1955                          1960                        1965 | 5904 | |
| gag gag tat aaa atg gca ctg tac aat ctc tat cca ggt gtt ttt<br>Glu Glu Tyr Lys Met Ala Leu Tyr Asn Leu Tyr Pro Gly Val Phe<br>1970                          1975                        1980 | 5949 | |
| gag aca gtg gaa atg tta cca tcc aaa gct gga att tgg cgg gtg<br>Glu Thr Val Glu Met Leu Pro Ser Lys Ala Gly Ile Trp Arg Val<br>1985                          1990                        1995 | 5994 | |
| gaa tgc ctt att ggc gag cat cta cat gct ggg atg agc aca ctt<br>Glu Cys Leu Ile Gly Glu His Leu His Ala Gly Met Ser Thr Leu<br>2000                          2005                        2010 | 6039 | |
| ttt ctg gtg tac agc aat aag tgt cag act ccc ctg gga atg gct<br>Phe Leu Val Tyr Ser Asn Lys Cys Gln Thr Pro Leu Gly Met Ala<br>2015                          2020                        2025 | 6084 | |
| tct gga cac att aga gat ttt cag att aca gct tca gga caa tat<br>Ser Gly His Ile Arg Asp Phe Gln Ile Thr Ala Ser Gly Gln Tyr<br>2030                          2035                        2040 | 6129 | |
| gga cag tgg gcc cca aag ctg gcc aga ctt cat tat tcc gga tca<br>Gly Gln Trp Ala Pro Lys Leu Ala Arg Leu His Tyr Ser Gly Ser<br>2045                          2050                        2055 | 6174 | |
| atc aat gcc tgg agc acc aag gag ccc ttt tct tgg atc aag gtg<br>Ile Asn Ala Trp Ser Thr Lys Glu Pro Phe Ser Trp Ile Lys Val<br>2060                          2065                        2070 | 6219 | |
| gat ctg ttg gca cca atg att att cac ggc atc aag acc cag ggt<br>Asp Leu Leu Ala Pro Met Ile Ile His Gly Ile Lys Thr Gln Gly<br>2075                          2080                        2085 | 6264 | |
| gcc cgt cag aag ttc tcc agc ctc tac atc tct cag ttt atc atc<br>Ala Arg Gln Lys Phe Ser Ser Leu Tyr Ile Ser Gln Phe Ile Ile<br>2090                          2095                        2100 | 6309 | |
| atg tat agt ctt gat ggg aag aag tgg cag act tat cga gga aat<br>Met Tyr Ser Leu Asp Gly Lys Lys Trp Gln Thr Tyr Arg Gly Asn<br>2105                          2110                        2115 | 6354 | |
| tcc act gga acc tta atg gtc ttc ttt ggc aat gtg gat tca tct<br>Ser Thr Gly Thr Leu Met Val Phe Phe Gly Asn Val Asp Ser Ser<br>2120                          2125                        2130 | 6399 | |

```
ggg ata aaa cac aat att ttt aac cct cca att att gct cga tac      6444
Gly Ile Lys His Asn Ile Phe Asn Pro Pro Ile Ile Ala Arg Tyr
    2135                2140                2145 atc cgt ttg cac cca act cat tat agc att cgc agc act ctt cgc      6489
Ile Arg Leu His Pro Thr His Tyr Ser Ile Arg Ser Thr Leu Arg
2150                2155                2160 atg gag ttg atg ggc tgt gat tta aat agt tgc agc atg cca ttg      6534
Met Glu Leu Met Gly Cys Asp Leu Asn Ser Cys Ser Met Pro Leu
    2165                2170                2175 gga atg gag agt aaa gca ata tca gat gca cag att act gct tca      6579
Gly Met Glu Ser Lys Ala Ile Ser Asp Ala Gln Ile Thr Ala Ser
    2180                2185                2190 tcc tac ttt acc aat atg ttt gcc acc tgg tct cct tca aaa gct      6624
Ser Tyr Phe Thr Asn Met Phe Ala Thr Trp Ser Pro Ser Lys Ala
    2195                2200                2205 cga ctt cac ctc caa ggg agg agt aat gcc tgg aga cct cag gtg      6669
Arg Leu His Leu Gln Gly Arg Ser Asn Ala Trp Arg Pro Gln Val
    2210                2215                2220 aat aat cca aaa gag tgg ctg caa gtg gac ttc cag aag aca atg      6714
Asn Asn Pro Lys Glu Trp Leu Gln Val Asp Phe Gln Lys Thr Met
    2225                2230                2235 aaa gtc aca gga gta act act cag gga gta aaa tct ctg ctt acc      6759
Lys Val Thr Gly Val Thr Thr Gln Gly Val Lys Ser Leu Leu Thr
    2240                2245                2250 agc atg tat gtg aag gag ttc ctc atc tcc agc agt caa gat ggc      6804
Ser Met Tyr Val Lys Glu Phe Leu Ile Ser Ser Ser Gln Asp Gly
    2255                2260                2265 cat cag tgg act ctc ttt ttt cag aat ggc aaa gta aag gtt ttt      6849
His Gln Trp Thr Leu Phe Phe Gln Asn Gly Lys Val Lys Val Phe
    2270                2275                2280 cag gga aat caa gac tcc ttc aca cct gtg gtg aac tct cta gac      6894
Gln Gly Asn Gln Asp Ser Phe Thr Pro Val Val Asn Ser Leu Asp
    2285                2290                2295 cca ccg tta ctg act cgc tac ctt cga att cac ccc cag agt tgg      6939
Pro Pro Leu Leu Thr Arg Tyr Leu Arg Ile His Pro Gln Ser Trp
    2300                2305                2310 gtg cac cag att gcc ctg agg atg gag gtt ctg ggc tgc gag gca      6984
Val His Gln Ile Ala Leu Arg Met Glu Val Leu Gly Cys Glu Ala
    2315                2320                2325 cag gac ctc tac                                                  6996
Gln Asp Leu Tyr
    2330
```

```
<210> SEQ ID NO 2
<211> LENGTH: 2332
<212> TYPE: PRT
<213> ORGANISM: homo sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80
```

-continued

```
Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495
```

```
His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Arg Ser Thr Arg
            740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
            770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
            850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910
```

```
Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305
```

```
Gln Arg Ser Lys Arg Ala Leu Lys Gln Phe Arg Leu Pro Leu Glu
1310            1315                1320

Glu Thr Glu Leu Glu Lys Arg Ile Ile Val Asp Asp Thr Ser Thr
1325            1330                1335

Gln Trp Ser Lys Asn Met Lys His Leu Thr Pro Ser Thr Leu Thr
1340            1345                1350

Gln Ile Asp Tyr Asn Glu Lys Glu Lys Gly Ala Ile Thr Gln Ser
1355            1360                1365

Pro Leu Ser Asp Cys Leu Thr Arg Ser His Ser Ile Pro Gln Ala
1370            1375                1380

Asn Arg Ser Pro Leu Pro Ile Ala Lys Val Ser Ser Phe Pro Ser
1385            1390                1395

Ile Arg Pro Ile Tyr Leu Thr Arg Val Leu Phe Gln Asp Asn Ser
1400            1405                1410

Ser His Leu Pro Ala Ala Ser Tyr Arg Lys Lys Asp Ser Gly Val
1415            1420                1425

Gln Glu Ser Ser His Phe Leu Gln Gly Ala Lys Lys Asn Asn Leu
1430            1435                1440

Ser Leu Ala Ile Leu Thr Leu Glu Met Thr Gly Asp Gln Arg Glu
1445            1450                1455

Val Gly Ser Leu Gly Thr Ser Ala Thr Asn Ser Val Thr Tyr Lys
1460            1465                1470

Lys Val Glu Asn Thr Val Leu Pro Lys Pro Asp Leu Pro Lys Thr
1475            1480                1485

Ser Gly Lys Val Glu Leu Leu Pro Lys Val His Ile Tyr Gln Lys
1490            1495                1500

Asp Leu Phe Pro Thr Glu Thr Ser Asn Gly Ser Pro Gly His Leu
1505            1510                1515

Asp Leu Val Glu Gly Ser Leu Leu Gln Gly Thr Glu Gly Ala Ile
1520            1525                1530

Lys Trp Asn Glu Ala Asn Arg Pro Gly Lys Val Pro Phe Leu Arg
1535            1540                1545

Val Ala Thr Glu Ser Ser Ala Lys Thr Pro Ser Lys Leu Leu Asp
1550            1555                1560

Pro Leu Ala Trp Asp Asn His Tyr Gly Thr Gln Ile Pro Lys Glu
1565            1570                1575

Glu Trp Lys Ser Gln Glu Lys Ser Pro Glu Lys Thr Ala Phe Lys
1580            1585                1590

Lys Lys Asp Thr Ile Leu Ser Leu Asn Ala Cys Glu Ser Asn His
1595            1600                1605

Ala Ile Ala Ala Ile Asn Glu Gly Gln Asn Lys Pro Glu Ile Glu
1610            1615                1620

Val Thr Trp Ala Lys Gln Gly Arg Thr Glu Arg Leu Cys Ser Gln
1625            1630                1635

Asn Pro Pro Val Leu Lys Arg His Gln Arg Glu Ile Thr Arg Thr
1640            1645                1650

Thr Leu Gln Ser Asp Gln Glu Glu Ile Asp Tyr Asp Asp Thr Ile
1655            1660                1665

Ser Val Glu Met Lys Lys Glu Asp Phe Asp Ile Tyr Asp Glu Asp
1670            1675                1680

Glu Asn Gln Ser Pro Arg Ser Phe Gln Lys Lys Thr Arg His Tyr
1685            1690                1695
```

```
Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
1925                1930                1935

Arg Ile Arg Trp Tyr Leu Leu Ser Met Gly Ser Asn Glu Asn Ile
1940                1945                1950

His Ser Ile His Phe Ser Gly His Val Phe Thr Val Arg Lys Lys
1955                1960                1965

Glu Glu Tyr Lys Met Ala Leu Tyr Asn Leu Tyr Pro Gly Val Phe
1970                1975                1980

Glu Thr Val Glu Met Leu Pro Ser Lys Ala Gly Ile Trp Arg Val
1985                1990                1995

Glu Cys Leu Ile Gly Glu His Leu His Ala Gly Met Ser Thr Leu
2000                2005                2010

Phe Leu Val Tyr Ser Asn Lys Cys Gln Thr Pro Leu Gly Met Ala
2015                2020                2025

Ser Gly His Ile Arg Asp Phe Gln Ile Thr Ala Ser Gly Gln Tyr
2030                2035                2040

Gly Gln Trp Ala Pro Lys Leu Ala Arg Leu His Tyr Ser Gly Ser
2045                2050                2055

Ile Asn Ala Trp Ser Thr Lys Glu Pro Phe Ser Trp Ile Lys Val
2060                2065                2070

Asp Leu Leu Ala Pro Met Ile Ile His Gly Ile Lys Thr Gln Gly
2075                2080                2085
```

-continued

```
Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330
```